United States Patent
Casterlin et al.

(12)

(10) Patent No.: US 6,372,515 B1
(45) Date of Patent: Apr. 16, 2002

(54) DEVICE FOR THE TESTING OF FLUID SAMPLES AND PROCESS FOR MAKING THE DEVICE

(75) Inventors: Douglas Casterlin, Hudson, NY (US); Henry J. Wells, Columbia, MD (US); Stan Cipkowski, Hudson, NY (US)

(73) Assignee: American Bio Medica Corporation, Kinderhook, NY (US)

( * ) Notice: Subject to any disclaimer, the term of this patent is extended or adjusted under 35 U.S.C. 154(b) by 0 days.

(21) Appl. No.: 09/295,095

(22) Filed: Apr. 21, 1999

Related U.S. Application Data (63) Continuation-in-part of application No. 08/981,665, filed on Nov. 5, 1997, which is a continuation-in-part of application No. 08/613,487, filed on Mar. 11, 1996, now Pat. No. 5,976,895.

(51) Int. Cl.[7] .............................................. G01N 33/533
(52) U.S. Cl. ........................... 436/518; 422/56; 422/57; 422/58; 422/59; 422/61; 422/62; 435/287.7; 435/287.8; 435/288.1; 435/969; 435/970; 435/805; 436/823; 436/810

(58) Field of Search .................. 422/56–62; 435/287.7, 435/287.8, 288.1, 969, 970, 805; 436/518, 823, 810

(56) References Cited

U.S. PATENT DOCUMENTS

| | | | | |
|---|---|---|---|---|
| 4,518,565 A | * | 5/1985 | Boger et al. | |
| 5,238,652 A | * | 8/1993 | Sun et al. | |
| 5,441,698 A | * | 8/1995 | Norell | |
| 5,500,375 A | * | 3/1996 | Lee-Own et al. | |
| 5,712,172 A | * | 1/1998 | Huang et al. | |

* cited by examiner

Primary Examiner—Bao-Thuy L. Nguyen
(74) Attorney, Agent, or Firm—Edmund M. Jaskiewicz (57) ABSTRACT

A test card for drugs of abuse has a thin flat member having the size and shape of a business card. A plurality of immunoassay test strips extend longitudinally from top to bottom at the card and are fastened side by side in parallel on one or both sides of the test card within the outline of the card. Each test strip is reactive to provide a visual indication in response to a particular drug of abuse. The test card thus provides for the simultaneous detection of multiple analytes. Processes are also disclosed for making the drug test card with test strips on one and both sides of the card.

7 Claims, 12 Drawing Sheets

DEVICE FOR THE TESTING OF FLUID SAMPLES AND PROCESS FOR MAKING THE DEVICE

RELATED APPLICATIONS

This is a continuation-in-part application of U.S. patent application Ser. No. 08/981,665 filed Nov. 5, 1997 which is a continuation-in-part of application Ser. No. 08/613,487 filed Mar. 11, 1996 now U.S. Pat. No. 5,976,895.

TECHNICAL FIELD

The present invention relates to the collection and testing of fluid samples for drugs of abuse, more particularly, to a multiple drug test card for indicating visually the presence of particular drugs of abuse in urine and a process for making the test card.

BACKGROUND ART

The increased availability and use of drugs of abuse by the general population has caused employers, governmental agencies, sports groups and other organizations to utilize drug screening both as a condition of employment and in order to maintain safety in the work place. Typical drug screening tests are performed for the purpose of quickly identifying on a qualitative basis the presence of drugs in a body fluid which may be urine. A complete analysis of the sample may then be carried out in a laboratory only if the preliminary screening results are positive. More and more such drug screenings are taking place on site or the work place and are generally carried out by testing personnel who are not technically trained, such as laboratory technicians. It is thus important that the drug screening procedure is simple but yet reliable. Further, the test apparatus must be such so as to enable the testing personnel to avoid all contact with the fluid specimen which is being tested.

Various forms of devices have been proposed for the collection and taking of body fluids, such as urine, which have proved to be cumbersome in operation since they involve a number of separate steps. Initially, the sample was collected and several additional steps were then required to transfer the urine sample to an analysis device. This multiple step procedure required the manual handling of the specimen through various devices and the use of such transfer devices inevitably caused spills which may result in contamination to the tester and surroundings. In addition, non-technical personnel who perform the screening tests on urine samples objected to coming into any kind of contact with the urine sample and even the handling of the sample itself.

Many of the known testing devices were rather complex in that they included a container for the specimen, and, subsequently it was necessary to transfer the specimen or at least a portion thereof to another compartment of the container in order to perform the test. This transfer of the specimen required vigorous shaking of the container or turning the container upside down in order to cause the flow of the specimen into a test compartment. It was therefore necessary to make the containers leak proof under such condition and the result was a complicated and expensive container structure.

Further, the containers incorporated the structure by means of which reagent strips were mounted in a test compartment of the container and which structure also enabled the fluid sample to flow into the test compartment into contact with the reagent strips. Such a mounting of the reagent strips further resulted in complicating the structure of the container since it was also necessary that provision be made to view the reagent strips from outside of the container. This was generally achieved by providing a transparent window or some other mounting of the reagent strips so as to be visible to testing personnel.

DISCLOSURE OF INVENTION

It is therefore the principal object of the present invention to provide a novel and improved device for the testing of body fluid samples, particularly urine, for several drugs of abuse at the same time.

It is a further object of the present invention to provide a novel and improved test card having a plurality of immunoassay test strips on one or both sides thereof with each strip being responsive to a particular drug of abuse and having a visual endpoint to indicate the presence or absence of a particular drug.

It is additional object of the present invention to provide a simple and effective process for making such a drug test card.

The objects of the present invention are achieved and the disadvantages of the prior art are eliminated by the drug abuse test device according to the present invention which may comprise a cup-like transparent container for retaining a urine sample to be tested. The open top of the container has a closure cover or cap and there is a diametrical slit in the cap. The slit is of such a size to accommodate a test card which has a plurality of immunoassay test strips mounted thereon in parallel on one side and each test strip is responsive to a particular drug of abuse. The test card is insertable through the slit so as to have one end immersed in the urine sample to a predetermined depth whereby the visual results of each test strip can be seen through the transparent wall of the container without removing the test card from the container so as to indicate the presence or absence of a particular drug of abuse in the urine sample. If the sample should test "positive" to indicate the presence of a drug in the urine, it is then necessary to send the sample to a certified laboratory for confirmatory testing. For this purpose, a second closure cap which is solid, i.e., not slit, is provided which may be threaded into the open end of the cup-like container. The test card is removed from the container, the solid closure cap is threaded on to close the container and the container is then ready for shipment to a laboratory.

As described above, the test kit includes a drug abuse test device for collecting and testing a urine sample. This test device comprises a cup-like container having a substantially transparent wall and having an open top upon which is threaded a closure cover provided with a slit therein to receive a test card. A solid second closure cap which threads over the outer end of the cup-like container is provided to seal the container to permit the safe shipment of a fluid sample therein.

The test kit also includes a screen test card for drugs of abuse which may comprise a thin flat member having the size and shape of a business card. A plurality of immunoassay test strips are fastened side by side in parallel on one or both sides of the test card within the outline of the card. Each test strip is reactive to provide a visual indication in response to a particular drug of abuse. The test card thus provides for the simultaneous detection of multiple analytes.

BRIEF DESCRIPTION OF THE DRAWINGS

Other objects and advantages of the present invention will be apparent upon reference to the accompanying description when taken in conjunction with the following drawings, which are exemplary, wherein.

MODES FOR CARRYING OUT THE INVENTION

Figures 1, 2:
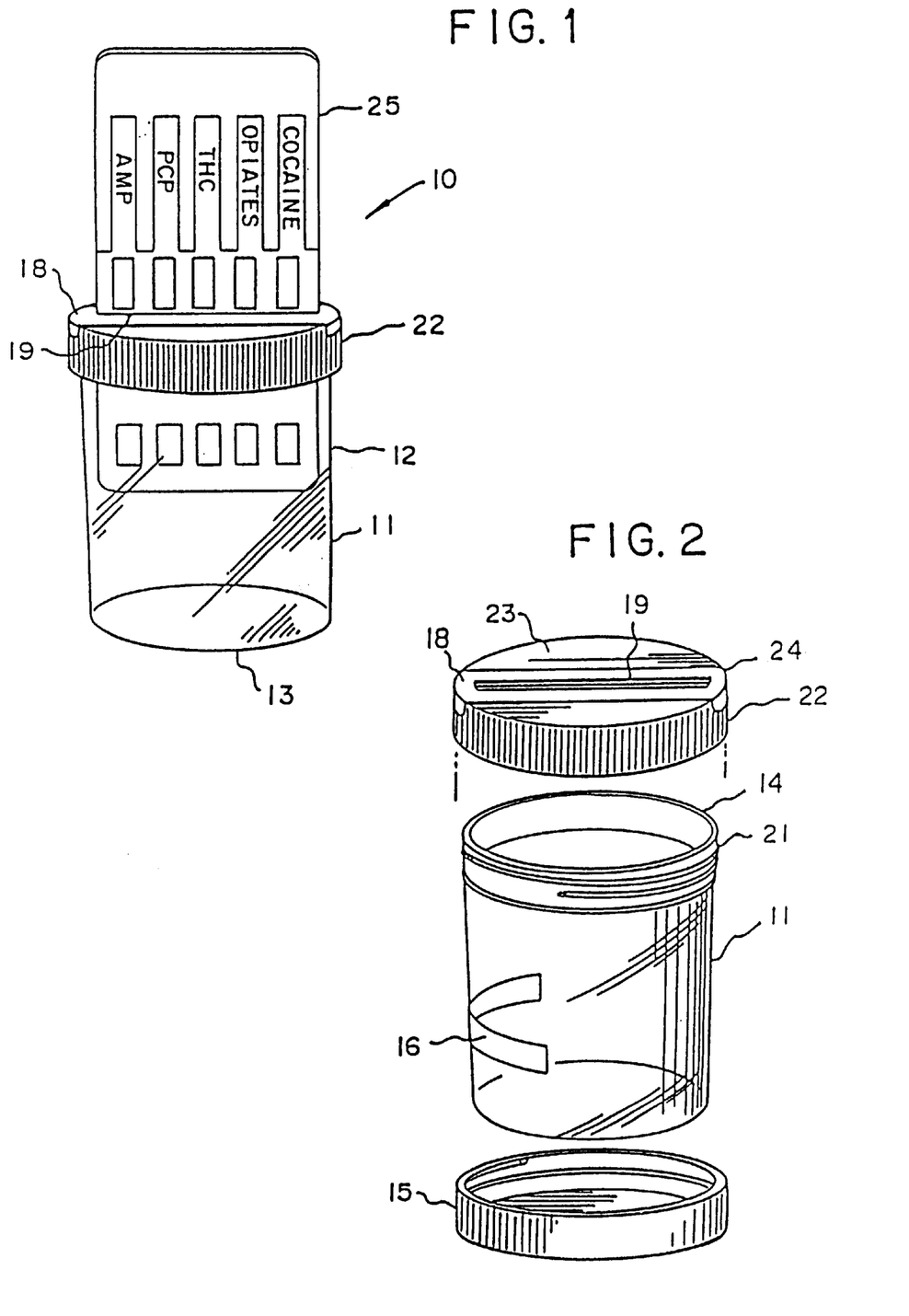
FIG. 1 is a perspective view of the drug abuse test kit according to the present invention generally showing the container, the test card partially inserted to the testing position in the container through a slit in the cover.
FIG. 2 is an exploded perspective view of the container according to the present invention for collecting and testing a fluid sample and generally showing the container, a cover having a slit covered with a removable adhesive seal and a second solid closure cap.

As may be seen in FIGS. 1 and 2, a drug abuse test kit according to the present invention is indicated generally at 10 and comprises a cup-like transparent test container or cup 11 having a cylindrical side wall 12, a closed bottom 13 and an open top 14. The cylindrical wall 12 may have a slight taper or be straight.

The open end 14 of the test cup 11 is provided with external threads 21 upon which is seated an outer closure cover or cap 22 provided with corresponding internal threads which are not shown in the drawing. The cover 22 has a circular top surface 23 from the periphery of which depends a cylindrical wall 24 on the inner surface of which there are provided internal threads. The cover surface 23 has a diametrical slit 19 therein shaped to accommodate a test card as will be presently described. There is also provided a solid cover or cap 15 which is similar in size and shape to the cover 22 but is solid or unslit so that the covers 15 and 22 may be interchangeably mounted on the open end 14 of the test cup 11. During shipment, the cover 15 is generally fitted on the bottom of the test cup. A temperature strip 16 is mounted on the bottom side wall of the test cup so as to be responsive to the temperature of the test sample within a test cup.

The cup container is essentially a specimen cup as commonly used in medicine and has a wall of material normally impervious to fluid specimens contained therein. The container may be formed or molded from any suitable material, such as a thermal plastic. It is preferred that the container is transparent since this enables the results from the test card to be read without removing the test card from the cup. But a transparent wall is not necessary and the wall may be translucent or even opaque. It is sufficient that the material have a degree of transparency such that one could distinguish the presence or absence of lines on the test portion of the test strips through the wall of the container when the test card is close to or even spaced from the container wall. While the cup shown is cylindrical, it is to be understood that other non-cylindrical shapes could be used.

A test card 25 which will indicate the presence or absence of any one of 5 different drugs of abuse is shown in FIG. 1 inserted within the slit 19 in the closure cap 22 and in further detail in FIGS. 3–6. The test card is of the multiple drug type in that test strips for five different drugs of abuse are mounted on the test card. The test strips 26–30 are spaced apart in parallel on a test side 31 of the test card and extend longitudinally of the test card from top to bottom thereof. These test strips indicate the presence or absence of the following specific drugs of abuse: PCP, cocaine, amphetamines (AMP), marijuana (THC) and opiates. Test strips 26–30 may be of the type as made by Bionike of South San Francisco, Calif., Phamatech of San Diego, Calif., Arista Biological of Bethlehem, Pa., and American BioMedica Corporation of Hudson, N.Y. Such test strips are characterized as immunoassay strips and employ colloidal gold chemistry. Each test strip is submerged up to a maximum line indicated at 32 and the results of the test are read in a test area indicated at 33. A blue line in the test area indicates "negative" or the absence of the particular drug in the test sample.

Figures 3, 4, 5:
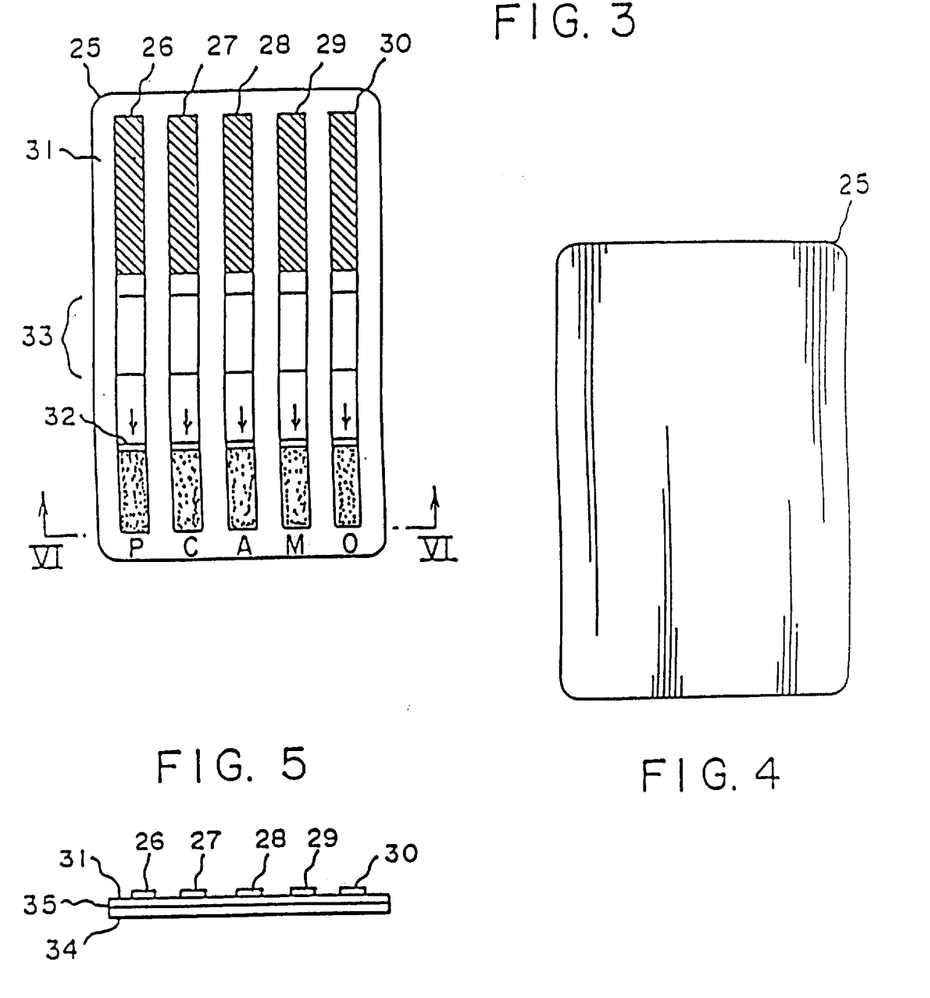
FIG. 3 is a plan view of the test side of a test card according to the present invention.
FIG. 4 is a plan view of the reverse side of the test card shown in FIG. 3.
FIG. 5 is an end elevational view of the test card shown in FIG. 3.
Figure 6:
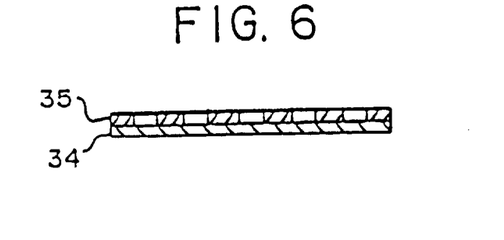
FIG. 6 is a sectional view taken along the line VI—VI of FIG. 3, but showing a modification wherein the test strips are flush with the top surface of the test card.
Figure 7:
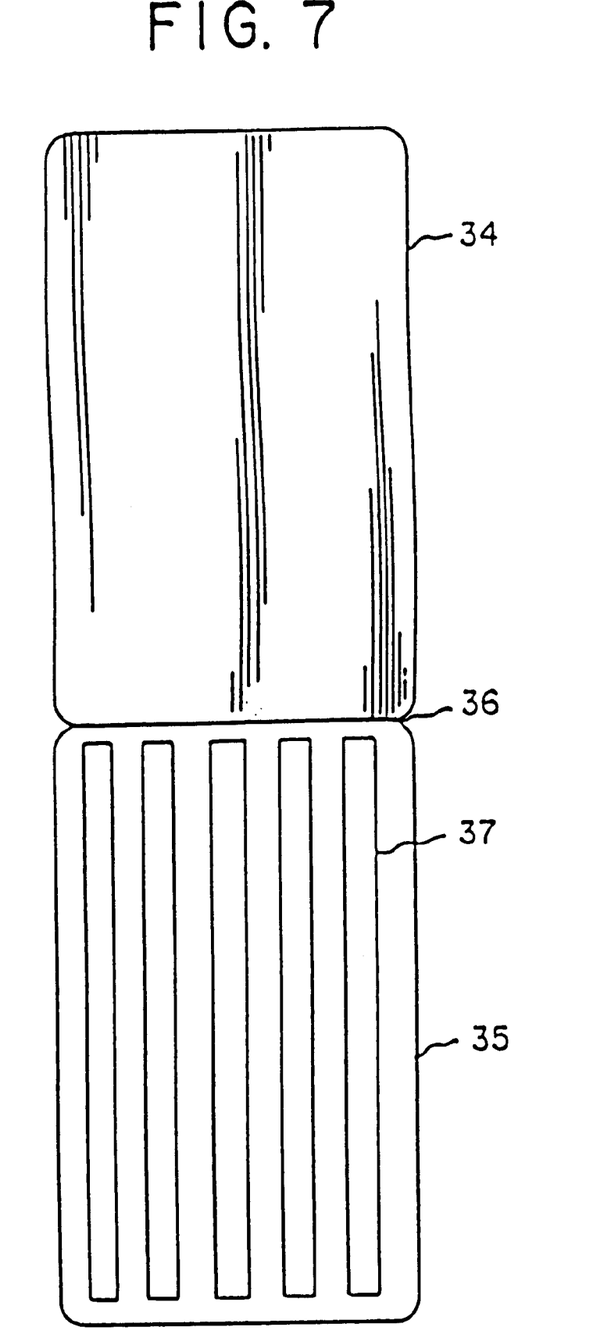
FIG. 7 is a plan view of the opened two piece test card before it is folded over to form the test card shown in FIGS. 3–6.

The test strips may be completely recessed as shown in FIG. 6 or partially recessed in the slots in the card so that portions of the test strip may project above the test surface 31 of the card as shown in FIG. 5. If the test strips are completely recessed, then the strips would be flush with the top surface of the top ply as shown in FIG. 6. The test card may be formed of two plys 34 and 35 as may be seen in FIG. 7 and these plys in turn are formed from a single strip having a bend or fold 36. The ply 35 is formed with a plurality of die cut slots 37 which are shaped and sized to receive each of the test strips. Thus, in the fabrication of a test card, the two portions 34 and 35 are folded over at end 36 and are adhered together. The test strips are then placed into the slots as shown in FIG. 6 and each of the test strips is adhered to the surface of the first portion 34 upon which the second portion 35 has been folded. In this modification the test strips are flush with the test surface 31.

It is also within the scope of this invention to make this test card of two separate or individual plys 34 and 35 which are then adhered together and the strips are fixed in the slots as described above.

In order to conduct a drug abuse test utilizing the test card according to the present invention a person being tested must first provide a urine specimen into the transparent test cup 11. The quantity of specimen provided must be such as to permit insertion of the test card up to about the maximum line indicated at 32. It is also possible to provide fill lines on the wall surface of the test container.

The test cup with a sufficient quantity of test specimen therein is then closed by threading the cap 22 on the top of the test cup. The cap 22 is provided with a readily removable adhesive sealing strip 18 which is placed over the slit 19. Thus, when the container with the test specimen is brought to the person conducting the test, the protective strip 18 is removed and the bottom end of the multiple drug test card 25 is inserted into the slit until the bottom of the test card rests upon the bottom of the test cup. Thirty to forty-eight (30–48)ml. of specimen will ensure that a sample receiving portion at the bottom end of the strip will be in contact with the specimen. The level of this quantity of fluid will be slightly below or above the fill line 32. The test card then remains in place for at least three minutes and the results of the test can be read on each individual test strip through the transparent wall of the container. Thus, if a line which may be reddish blue or pink appears on any one of the test strips, this indicates "negative" and the absence of that particular drug of abuse in the test specimen. With such a negative result, the urine sample and the container are discarded. If no such line appears, then the presence of any of the five drugs of abuse from the specimen is indicated.

However, when the results of the test are positive, it is preferable to send the specimen to a certified laboratory for a confirmatory analysis by more specific methods of testing such as gas chromatography or mass spectrometry. In order to ship the sample in the container, the closure 22 is removed and the solid cover 15 is threaded down tightly upon the open end of the container.

Figure 8:
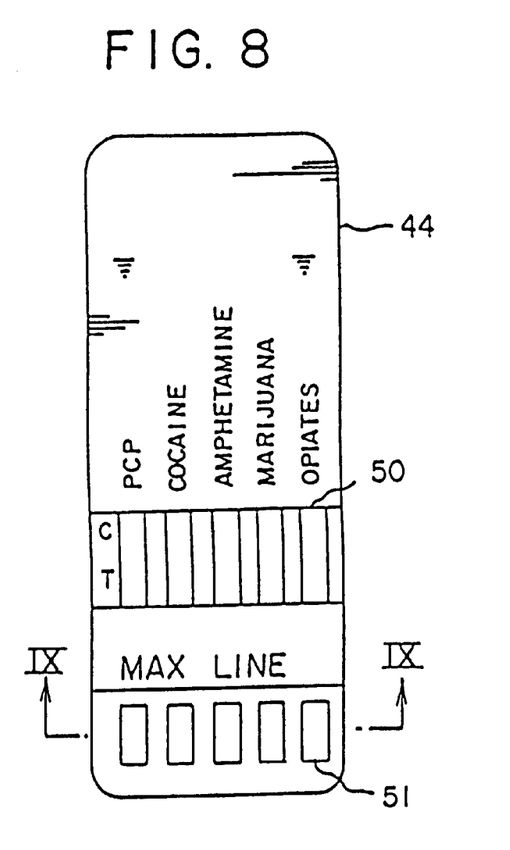
FIG. 8 is a plan view of another modification of the test card.
Figure 9:
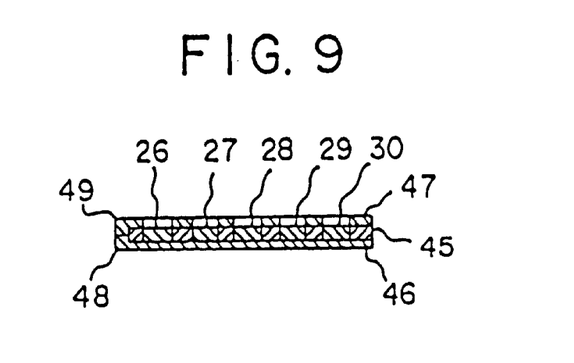
FIG. 9 is a sectional view taken along the line IX—IX of FIG. 8.
Figure 10:
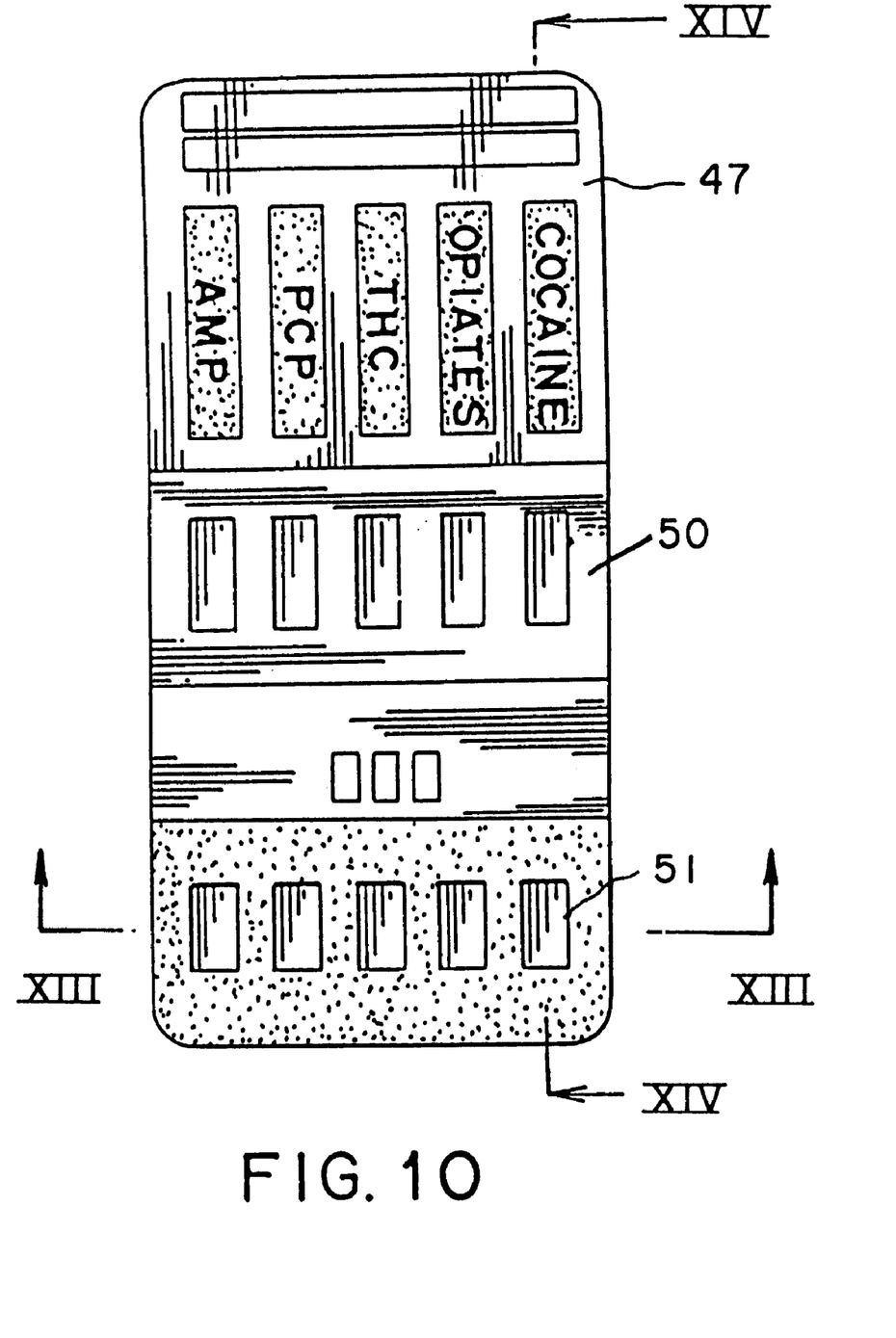
FIG. 10 is a plan view of the test side of a further modification of the test card.

A modification of the test card is shown at 44 in FIG. 8. In this modification, the test strips are covered but the pertinent test and sample portions of the test strips are exposed through openings. The test card 44 comprises a central ply 45 of styrene which has a thickness of 1.25 mm. corresponding to or slightly greater than the thickness of the test strips and slots are provided in the center ply to receive the test strips. The top and bottom faces of the central ply 45 are covered by a bottom ply 46 and a top ply 47 which may be made from a single piece of material double scored at 48 and 49 so as to wrap around the central ply 45 in the manner as shown in FIG. 10. The top and bottom plys may be of a thin vinyl sheet or cardboard coated with plastic. The top ply 47 is provided with a plurality of test windows 50 through which the test results as indicated by the test strips can be seen. At the lower or bottom end of the card are provided sample openings 51 through which the liquid test specimen is able to contact the absorbent or sample receiving portions of the test strips.

In FIGS. 10–16 there is shown a modification of the test card 44 in which the card is made of three separate plys which are then laminated. The bottom and top plys 46 and 47 are made of a thin vinyl sheet having a thickness of 0.33 mm. And the center ply 45 is made of styrene having a thickness of about 1.25 mm. The top ply 47 similarly has the test openings or windows 50 and the sample receiving openings 51 and the bottom ply 46 is solid as shown.

Figures 11, 12, 13:
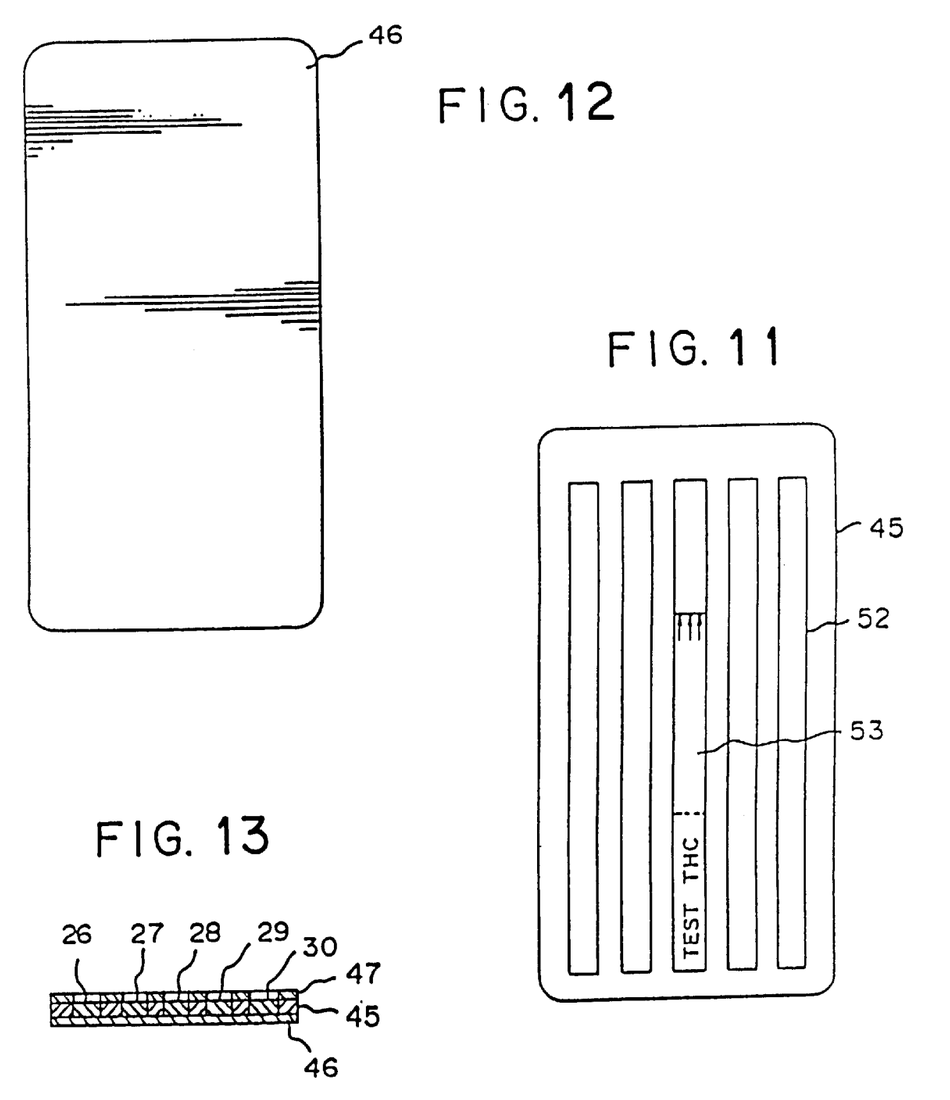
FIG. 11 is a plan view of the center ply of the test card of FIG. 10 and showing a test strip in a slot thereof.
FIG. 12 is a plan view of the reverse side of the test card of FIG. 10.
FIG. 13 is a sectional view taken along the line XIII—XIII of FIG. 10.
Figures 14, 16:
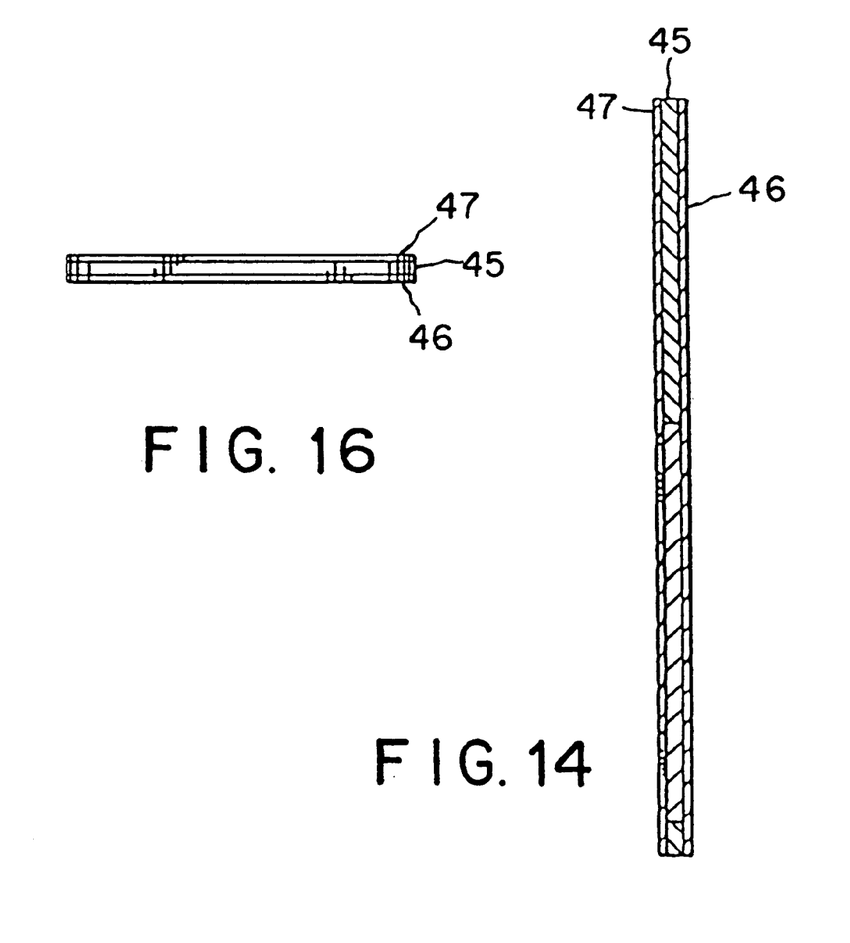
FIG. 14 is a sectional view taken along the line XIV—XIV of FIG. 10.
FIG. 16 is an end view of the test card shown in FIG. 10.
Figure 15:
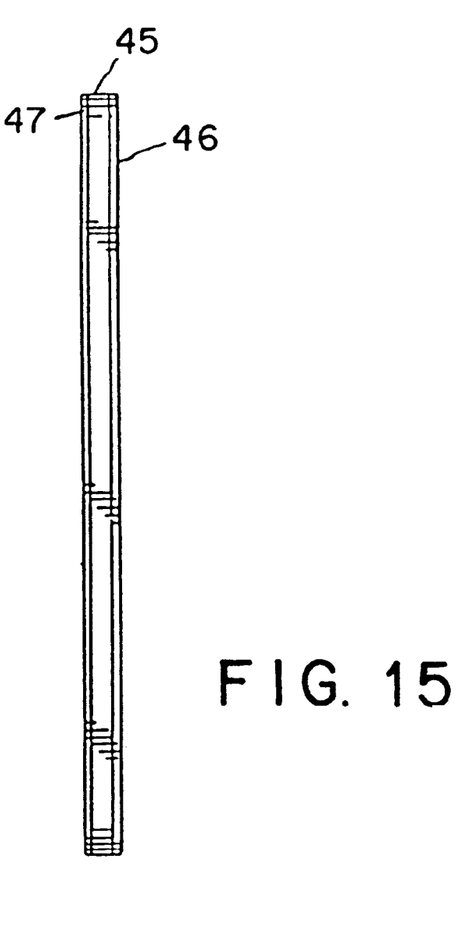
FIG. 15 is a side elevational view of the test card shown in FIG. 10.

The central ply 45 is provided with a plurality of longitudinally extending slots 52 and a test strip 53 is seated in each of these slots as shown. The test strip generally has a length less than that of the slot 52. In this embodiment, only a single test strip for THC (marijuana) is shown. While this embodiment of the test card has provision for five test strips, it is to be understood that the card can be made in the same manner with less than five strips and even a single strip if so desired. In such a modification, the windows 50 and 51 for the omitted strips are usually solid.

Figure 17:
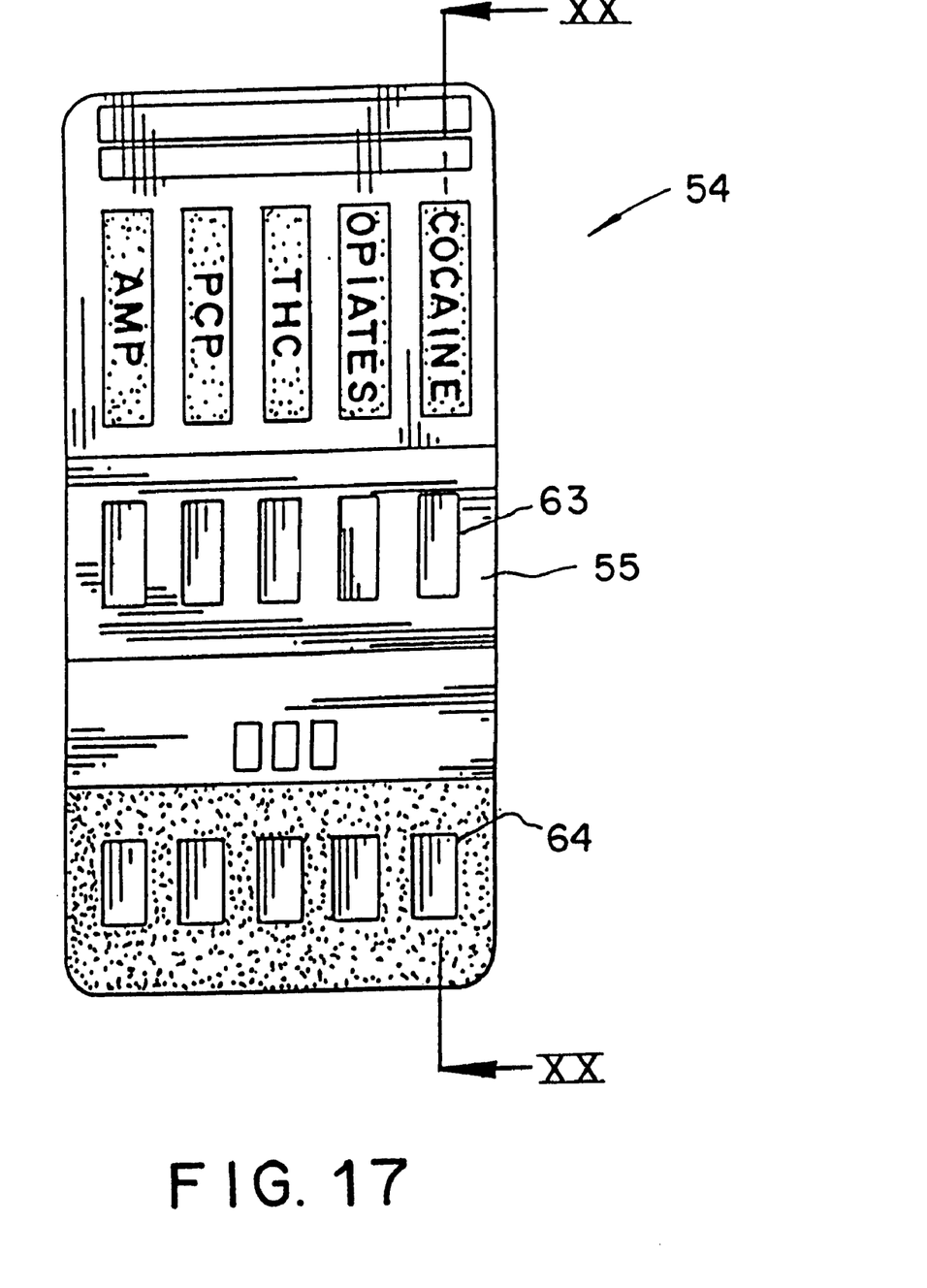
FIG. 17 is a plan view of a further modification of the test card.
Figure 18:
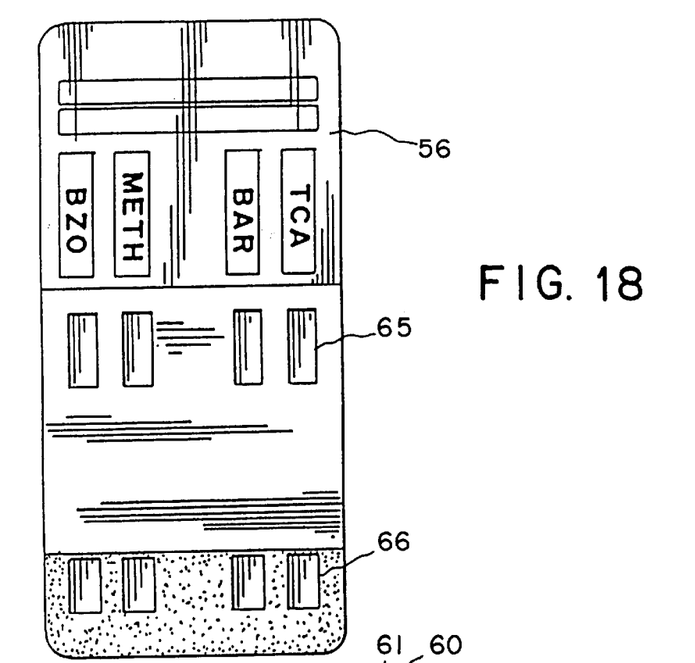
FIG. 18 is a plan view of the reverse side of the test card of FIG. 17.
Figure 22:
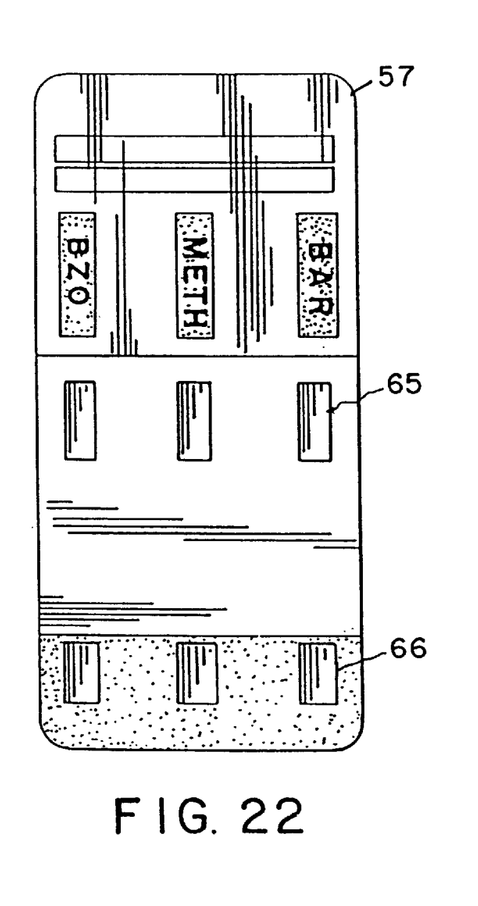
FIG. 22 is a plan view of further modifications of the reverse side of the test card of FIG. 17.
Figure 23:
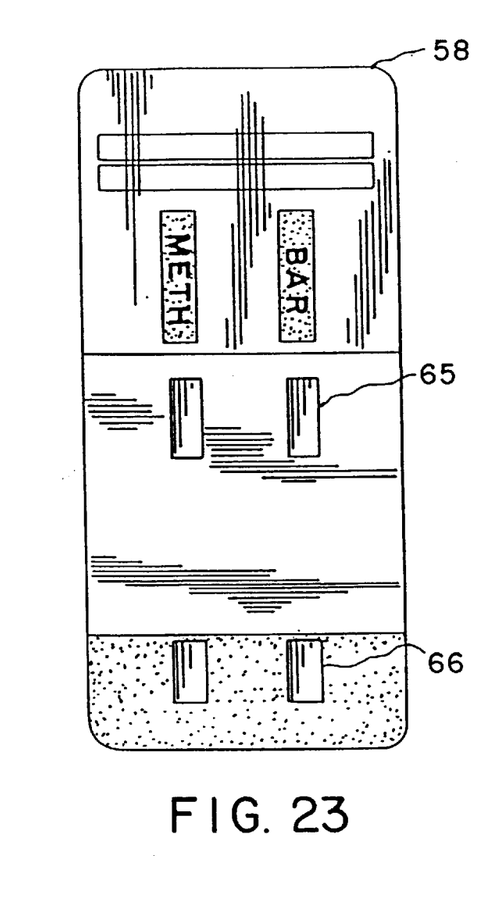
FIG. 23 is a plan view of further modifications of the reverse side of the test card of FIG. 17.
Figure 24:
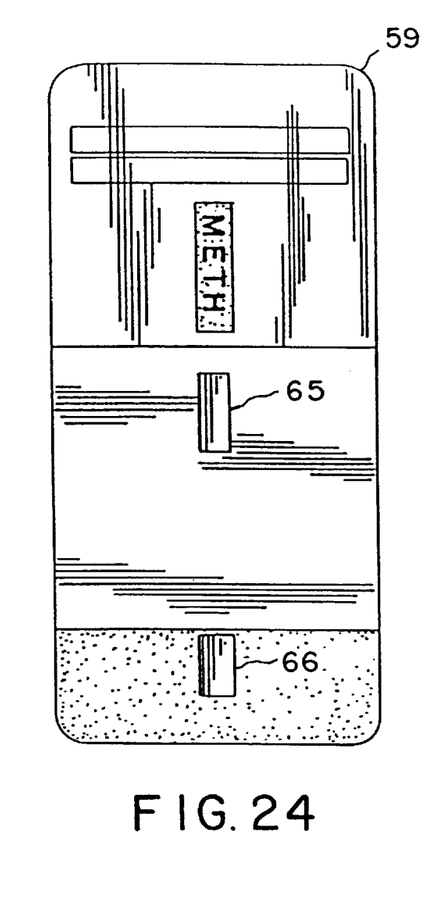
FIG. 24 is a plan view of further modifications of the reverse side of the test card of FIG. 17.

Proceeding next to FIG. 17, there is shown at 54 a test card modification which has test strips on both sides thereof to increase the number of different drugs which can be tested while maintaining the same overall size and configuration of the test card. Test card 54 has a front face or surface 55 which is the same front face 47 of the test card shown in FIG. 10. However, the reverse side of this test card is shown at 56 in FIG. 18 and has an additional number of test strips thereon as shown. The number of test strips mounted on the reverse side of the test card may vary as shown in the rear faces of the test cards 57, 58 and 59 illustrated in FIGS. 22, 23, and 24 respectively.

Figures 19, 20:
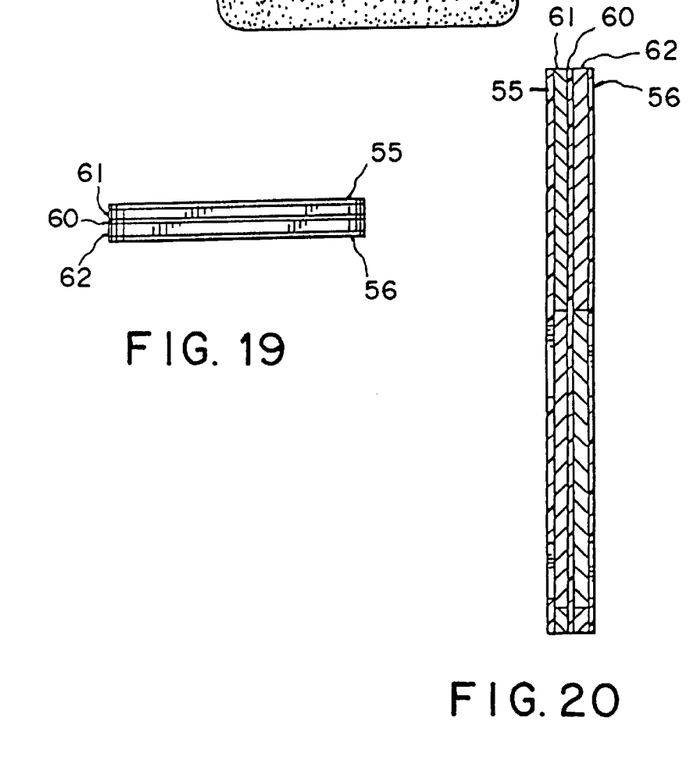
FIG. 19 is an end view of the test card of FIG. 17.
FIG. 20 is a sectional view taken along the line XX—XX of FIG. 17.
Figure 21:
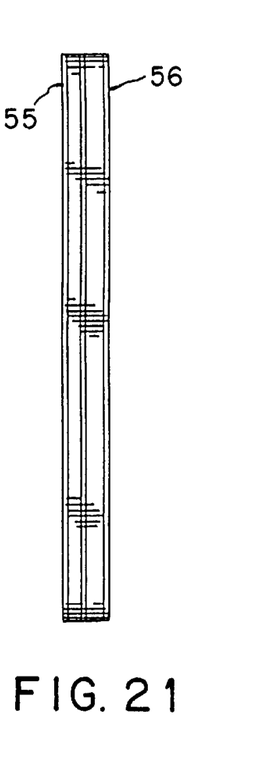
FIG. 21 is a side elevational view of the test card of FIG. 17.

The test card 54 has the front and back plys or faces 55 and 56, a central ply 60 and intermediate plys 61 and 62. These intermediate plys are similar to the center ply 45 shown in FIG. 11. These plys and panels are all adhered together as shown in FIGS. 19–21.

For purposes of efficiency, intermediate plys 61 and 62 would be the same as center ply 45 but only one or more of the slots 52 in the intermediate plys may be assembled with a test strip therein. Thus, five appropriate test strips 53 would be assembled in the intermediate ply 61 to correspond with the drugs of abuse as shown in FIG. 17 and one or more of these test strips would be assembled in intermediate ply 62 to correspond to the drugs as illustrated in the rear plys 56 in FIGS. 18 and 22–24.

The front panel 55 is provided with a plurality of test openings 63 and a plurality of windows or sample receiving openings 64. These openings are positioned to correspond with the visual test portions and sample receiving portions of a test strip 53. In a like manner, each of the rear panels 56–59 is provided with the appropriate number of test windows 65 and sample receiving windows or openings 66.

The central ply 60 is imperforate so as to maintain separation between the test strips in the intermediate plys 61 and 62.

Figure 25:
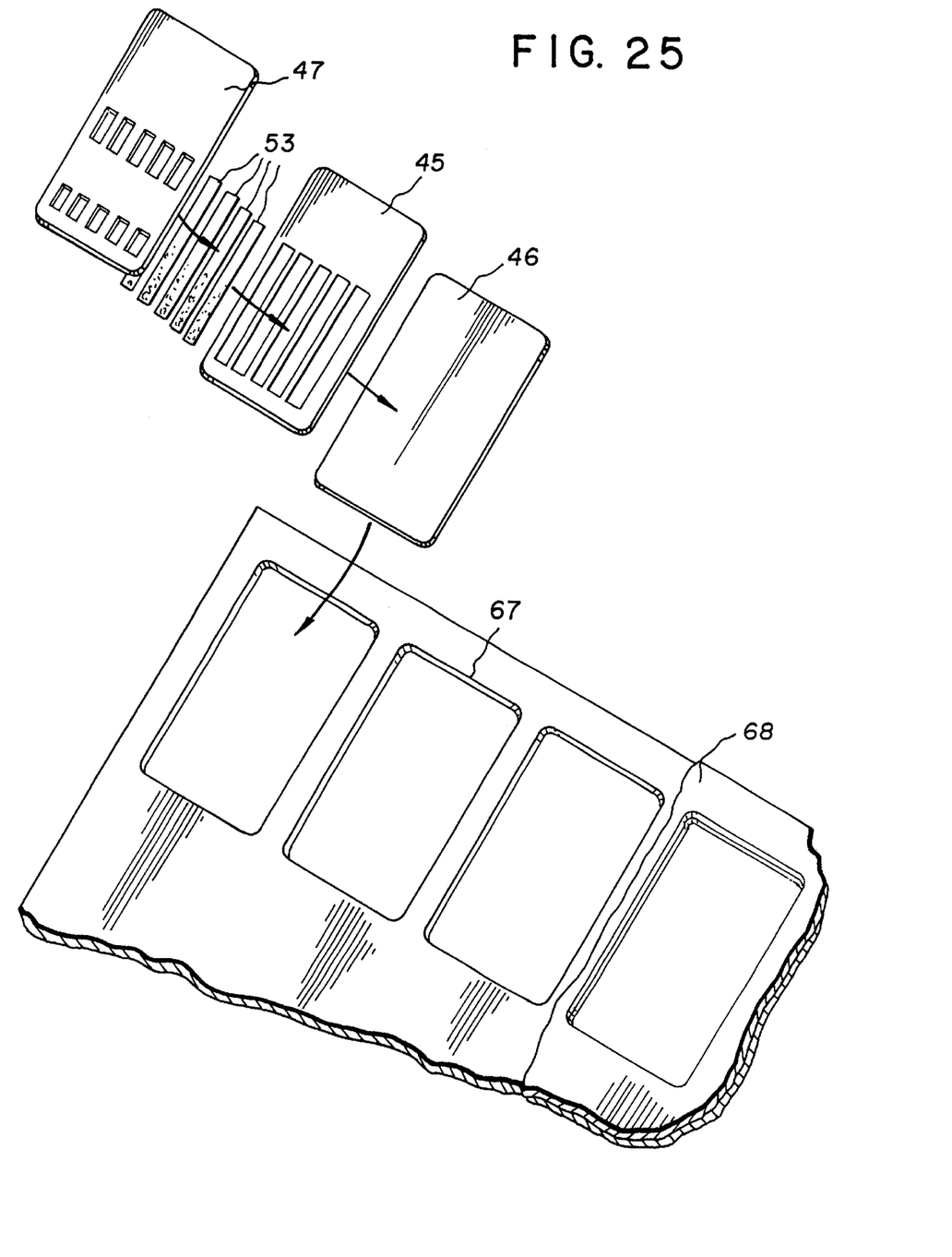
FIG. 25 is a schematic view illustrating the assembly of the test card using a template.

In the process of making or assembling a drug test card having test strips on a single side such as card 54 shown in FIG. 17, the back panel 46 is fixed in position by placing the card in an appropriately configured recess 67 in a template or jig 68. The recess 67 is of a depth sufficient to accommodate the central ply 45 and the top ply 55 so that the recess effectively aligns the components of the test card in their proper positions. The template 68 may have one or more recesses 67. The back panel 46 may be positioned in the recess 67 by hand or by machinery.

A middle panel such as 45 in FIG. 11 is then positioned on the seated back panel 46 and adhered thereto. This central panel will have the longitudinally extending side-by-side parallel slots therein and an immunoassay test strip is then positioned in one or more of these slots. Subsequently, the front panel 55 is then positioned over the middle or center panel 45 to enclose the test strips therein. The front panel 55 has the appropriate test window 63 and sample receiving window 64 therein as described above. The assembled test card having test strips on one face thereof is then removed from the template.

In order to make a two sided test card, such as illustrated in FIGS. 18 and 22–24, the assembled test card as described above is turned over and repositioned in the recess so that the front face or panel 55 is seated in the template. Subsequently, a second middle or central ply 45 which has adhesive on both faces thereof is positioned on the back panel 46 and additional test strips placed in the slots of this second middle panel. A third panel which then forms a rear face 56–59 of the two sided test card is then adhered to the second middle panel. The completed two sided test card which will appear as shown in FIGS. 19 and 21 when viewed from the side or edge will then be completed and removed from the template.

Figure 26:
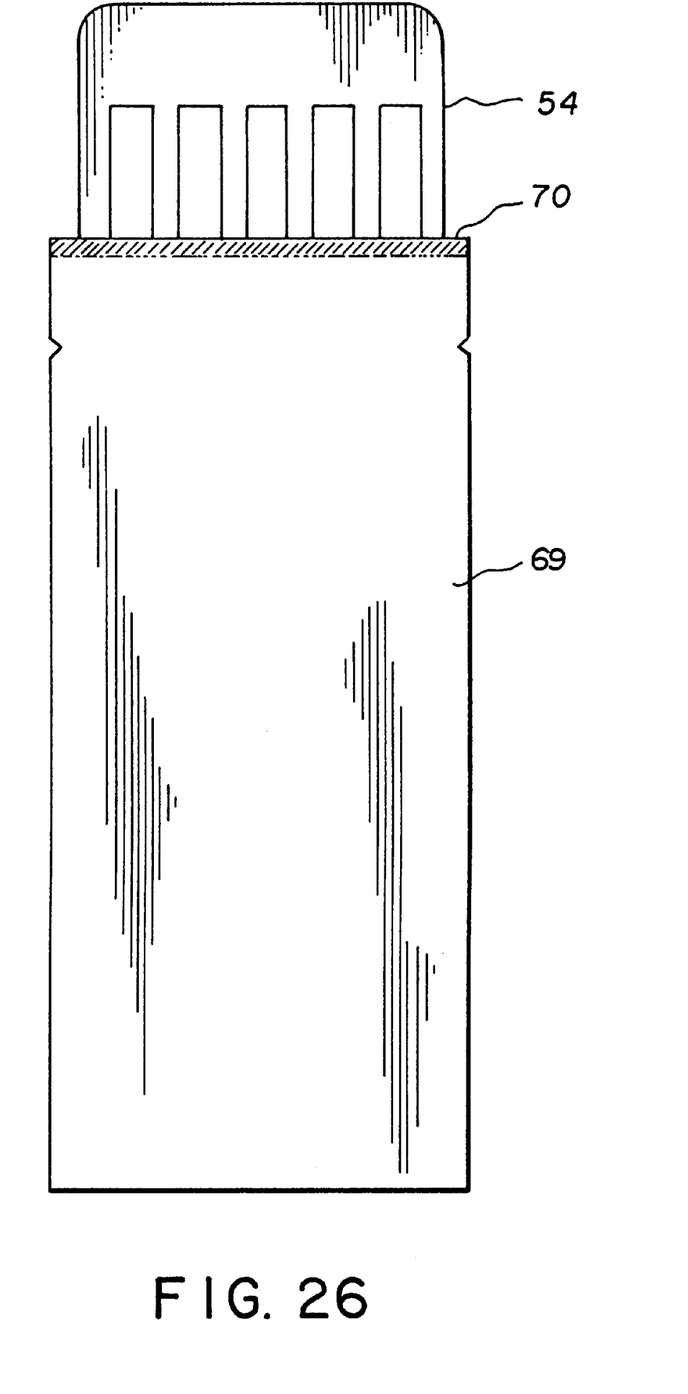
FIG. 26 is a plan view of a foil pouch with a test card partially inserted therein.

In order to protect the test card during shipment and to prevent any deterioration of the test strips from the atmosphere, the test card such as 54 shown in FIG. 26 is inserted into a appropriately shaped foil pouch 69. The top 70 of the pouch 69 is then sealed to enclose the card completely therein and may be stamped with the expiration date or any other information which is deemed appropriate.

Each of the test strips 26–30 and 53 is a one-step immunoassay in which a specially labeled drug, (drug conjugate) competes with drug which may be present in the sample for the limited number of binding sites on an antibody. The test strip consists of a membrane strip onto which a drug conjugate has been immobilized. A colloidal gold-antibody complex is dried at one end of the membrane. In the absence of any drug in the urine sample, the colloidal gold-antibody complex moves with the urine sample by capillary action to contact the immobilized drug conjugate. An antibody-antigen reaction occurs forming a visible line in the test area. The formation of a visible line in the test area occurs when the test is negative for the drug. Thus, a single test line indicates that the sample contains either no analyte or its presence is below the cut-off level. When a drug is present in the urine sample, the drug or its metabolite will compete with the immobilized drug conjugate in the test area for the limited antibody sites on the colloidal gold-labeled antibody complex. If a sufficient amount of drug is present, it will fill all of the available binding sites, thus preventing attachment of the label antibody to the drug conjugate. An absence of a color line or band in the test area is indicative of a positive result. A control band or line comprised of a different antibody/antigen reaction is present on the membrane strip. The control line is not influenced by the presence or absence of drug in the urine and therefore should be present in all reactions.

In summary, if a single band appears in the control zone and no band appears in the test zone then the results are "positive" which indicates that that particular drug is present above a predetermined level which will range from 25–1000 ng./ml., depending on the particular drug involved. If two color bands appear, one in the control region and the other in the test region then the test results are "negative" which indicates that the level of that particular drug is below the predetermined detection of sensitivity.

In the event that there are no distinct color bands visible in both the test zone and the control zone or if there is a visible band in the test zone but not in the control zone, then the result is invalid and retesting of the specimen is recommended with another test card.

The test card can also be used as a carrier or delivery system for a biological detection or monitor device by replacing the drug test strips with strips treated with suitable chemicals so as to be responsive to different and selected biological warfare agents. The strips would then function similarly to drug abuse strips to provide a visual indication of the presence in a predetermined quantity of a specific biological warfare agent or the absence of such an agent.

INDUSTRIAL APPLICABILITY

Thus it can be seen that the present invention discloses a novel and improved drug abuse test kit which comprises a container for the fluid specimen being tested and a multiple drug test card which is inserted in the specimen within the container and the visual results of the test are read on the test card through the wall of the container. The test card thus comprises a number of individual test strips of the immunoassay type and each strip is responsive or indicative to a particular drug of abuse. The test card may be made of plastic coated cardboard or thin sheets of plastic which are laminated together. This drug abuse test kit enables one to obtain rapidly a visual, qualitative result which is very advantageous for forensic purposes but is not limited to such purposes.

It will be understood that this invention is susceptible to modification in order to adapt it to different usages and conditions, and accordingly, it is desired to comprehend such modifications within this invention as may fall within the scope of the appended claims.

What is claimed is:

1. A multiple drug test card for the testing of fluid samples for drugs of abuse comprising a thin flat member having a rectangular outline and having front and rear surfaces and first and second ends, one or more immunoassay test strips disposed side-be-side adjacent said front surface in a longitudinal direction extending between said first and second ends and one or more immunoassay test strips disposed side-by-side in said longitudinal direction adjacent said rear surface, said test strips each having thereon immunoassay means to indicate visually the presence or absence of a selected drug of abuse, means on said thin flat member for separating said front and rear surface test strips, said test strips each having a first end having a sample receiving portion and a test portion spaced longitudinally therefrom wherein, in use, the fluid sample moves by capillary action to the test portion at which the presence or absence of a selected drug of abuse in the fluid sample is visually indicated, the first ends of said test strips disposed at the first end of said thin flat member but spaced therefrom, said test strips each having on other end spaced from the second end of said thin flat member, said front and rear surfaces of said thin flat member each having one or more openings therein to register with and expose each of the sample receiving and test portions of each of the one or more test strips adjacent said respective front and rear surfaces.

2. A multiple drug test card as claimed in claim 1 wherein said separating means comprises a central ply, a first intermediate ply sandwiched between said central ply and a top ply to define said front surface and a second intermediate ply sandwiched between said central ply and a bottom ply to define said rear surface, said front surface test strips disposed in said first intermediate ply and said rear surface test strips disposed in said second intermediate ply.

3. A multiple drug test card as claimed in claim 2 wherein there are one or more side-by-side parallel longitudinally extending slots in each of said first and second intermediate plys and said slots having both ends thereof closed and spaced from the respective first and second ends of said thin flat member, one or more test strips seated within a respective slot.

4. A multiple drug test card as claimed in claim 2 wherein said one or more openings comprise pairs of openings in said top and bottom plys corresponding to the plurality of test strips in an adjacent one of said first or second intermediate plys.

5. A multiple drug test card as claimed in claim 2 wherein said central ply is imperforate.

6. A multiple drug test card as claimed in claim 2 wherein said test strips each has a thickness substantially equal to the thickness of a respective intermediate ply.

7. A multiple drug test card as claimed in claim 1 wherein there is a single test strip in said second intermediate ply.

* * * * *